(12) United States Patent
Hotamisligil et al.

(10) Patent No.: US 7,232,897 B2
(45) Date of Patent: Jun. 19, 2007

(54) COMPOSITIONS AND METHODS FOR MODULATING NH2-TERMINAL JUN KINASE ACTIVITY

(75) Inventors: Gokhan S. Hotamisligil, Wellesley, MA (US); Michael Karin, La Jolla, CA (US); Lufen Chang, La Jolla, CA (US)

(73) Assignee: Harvard University, President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/475,505

(22) PCT Filed: Apr. 24, 2002

(86) PCT No.: PCT/US02/12687

§ 371 (c)(1),
(2), (4) Date: May 3, 2004

(87) PCT Pub. No.: WO02/085396

PCT Pub. Date: Oct. 31, 2002

(65) Prior Publication Data

US 2005/0261247 A1 Nov. 24, 2005

Related U.S. Application Data

(60) Provisional application No. 60/285,966, filed on Apr. 24, 2001.

(51) Int. Cl.
*C07H 17/08* (2006.01)
*A61K 31/00* (2006.01)

(52) U.S. Cl. ............... 536/7.4; 530/303; 514/1; 514/585

(58) Field of Classification Search ............ 424/94.5, 424/115
See application file for complete search history.

(56) References Cited

U.S. PATENT DOCUMENTS

| | | | |
|---|---|---|---|
| 5,498,631 A | | 3/1996 | Gorbach et al. |
| 5,506,211 A | | 4/1996 | Barnes et al. |
| 5,837,244 A | * | 11/1998 | Karin et al. ............ 424/139.1 |
| 5,877,309 A | * | 3/1999 | McKay et al. ............ 536/24.5 |
| 6,043,083 A | * | 3/2000 | Davis et al. ............ 435/325 |

OTHER PUBLICATIONS

Schroder AK et al. 2004. Insulin resistance in patients with polycystic ovary syndrome. Ann Med. 36:426-39.*
Yee B et al. 2004. Neuroendocrine changes in sleep apnea. Curr Opin Pulm Med. 10:475-81.*
Choudhury J et al. 2004. Clinical aspects of fatty liver disease. Semin Liver Dis 24: 349-62.*
Musso C et al. 2004. Clinical course of genetic diseases of the insulin receptor (type A and Rabson-Mendenhall syndromes): a 30-year prospective. Medicine 83: 209-22.*
Ness-Abramof R et al. 2004. Medical therapy for obesity: present and future. Isr Med Assoc J 6: 760-5.*
Segal R. 2004. Type 2 diabetes and disease management: exploring the connections. Dis Manag 7 Suppl 1: S11-22.*
Muhammad S. 2004. Epidemiology of diabetes and obesity in the United States. Compend Contin Educ Dent 25: 195-8, 200, 202, 204.*
Bogoyevitch MA et al. 2004. Targeting the JNK MAPK cascade for inhibition: basic science and therapeutic potential. Biochim Biophys Acta 1697: 89-101.*
Plourde G. 2006. Preventing and managing pediatric obesity. Canadian Family Physician 52: 322-328.*
Bennett BL. 2003. JNK: a new therapeutic target for diabetes. Curr Opin Pharmacol 3: 420-425.*
Jaeschke, Anja et al., "An essential role of the JIP1 scaffold protein for JNK activation in adipose tissue," Genes & Development 18:1976-1980 (2004).
Jaeschke Anja et al., "Disruption of the Jnk2 (Mapk9) gene reduces destructive insulitis and diabetes in a mouse model of type I diabetes," PNAS 2005 102:6931-6935 (2005).
Kaneto, Hideaki et al., "Possible novel therapy for diabetes with cell-permeable JNK-inhibitory peptide," Nature Medicine 10:1128-1132 (2004).
Nakatani, Yoshihisa et al., "Modulation of the JNK Pathway in Liver Affects Insulin Resistance Status," J. of Biological Chemistry 279:45803-45809 (2004).
Hirosumi, Jiro et al. "A central role for JNK in obesity and insulin resistance," Nature 420:353-356 (2002).

* cited by examiner

*Primary Examiner*—Sandra E. Saucier
*Assistant Examiner*—Lora E Barnhart
(74) *Attorney, Agent, or Firm*—Edwards Angell Palmer & Dodge LLP; Peter C. Lauro, Esq.

(57) ABSTRACT

Disclosed herein are compositions and methods used to modulate a $NH_2$-terminal Jun Kinase activity. These compositions and methods can be employed to regulate metabolic disorders associated with, for example, insulin such as diabetes. The reduction in $NH_2$-terminal Jun Kinase activity can lead to the reduction in weight and improve insulin sensitivity.

10 Claims, 16 Drawing Sheets

FIG. 5A Kinase Assay
FIG. 5B Immunoblot

Jnk2 -/-

Jnk1 -/-

WT

H&E

Oil-Red-O

COMPOSITIONS AND METHODS FOR MODULATING NH2-TERMINAL JUN KINASE ACTIVITY

TECHNICAL FIELD

The present application is a US national phase application, pursuant to 35 U.S.C. §371, of PCT international application Ser. No. PCT/US02/12687, filed Apr. 24, 2002, designating the United States and published in English as publication WO02/085396 on Oct. 31, 2002, which claims priority to and the benefit of US provisional application Ser. No. 60/285,966, filed Apr. 24, 2001.

BACKGROUND OF THE INVENTION

An estimated one-half of adults in the country are either overweight or obese. Obesity can lead to a greater risk for developing a host of diseases, including diabetes, heart disease, stroke and certain cancers. Patients with non-insulin dependent diabetes mellitus (NIDDM) may develop insulin resistance and impaired glucose tolerance.

SUMMARY

The invention is based on the discovery that reduced expression of a NH2-terminal Jun Kinase (JNK), e.g., JNK1, leads to reduced weight and improved insulin sensitivity. Accordingly, the invention features a method of treating a metabolic disorder associated with insulin resistance by administering to a mammal an inhibitor of JNK.

The mammal, e.g., a human patient, is identified as being obese or at risk of becoming obese. By "obese" is meant having an excess amount of adipose tissue. Standard clinical tests are used to determine whether an individual is obese, e.g., by calculating relative weight or body mass index (BMI) for an individual and comparing the values to a predetermined standard of ideal or desirable relative weight or BMI. For example, assessment of skin fold thickness over various areas of the body is taken into consideration together with height, weight, and age to determine the amount of adipose tissue content in an individual. Excess of adipose tissue content is determined by comparing the value against average (or standard) values for an individual of comparable age. For example, a 20% increase in mean relative weight or a BMI above the 85$^{th}$ percentile for young adults constitutes a health risk and may indicate therapeutic intervention, e.g., treatment with a JNK inhibitor. The inhibitors are also administered to individuals who are not obese, but wish to reduce their weight.

The mammal is identified as suffering from diabetes, is at risk of developing diabetes, suffering from insulin resistance, or at risk of developing insulin resistance. The term "diabetes," includes both insulin-dependent diabetes mellitus (i.e., IDDM, also known as type I diabetes) and non-insulin-dependent diabetes mellitus (i.e., NIDDM, also known as Type II diabetes). Preferably, the mammal is suffering from or at risk of developing Type II diabetes.

JNK inhibitors are compounds, which reduce the enzymatic activity of a JNK, e.g., JNK1 or JNK2, or expression of a JNK isotype. For example, compounds, which inhibit JNK enzymatic activity, bind to an ATP binding site in JNK or bind to a catalytic domain of JNK. The compound preferentially inhibits JNK1 compared to JNK2 or other JNK isotypes. Alternatively, the compound inhibits JNK2 or both JNK1 and JNK2. For example, the compound is SP600125. Compounds, e.g., polypeptides, organic compounds, or inorganic compounds, are isolated or purified. An "isolated" or "purified" composition is substantially free of cellular material or other contaminating proteins from the cell or tissue source from which it is derived, or substantially free from chemical precursors or other chemicals when chemically synthesized. A polypeptide that is substantially free of cellular material includes preparations of the polypeptide in which the polypeptide is separated from cellular components of the cells from which it is isolated, e.g., the polypeptide is recombinantly produced. Preferably, a preparation of a therapeutic compound, e.g., a JNK inhibitor, is at least 75%, more preferably 80%, more preferably 85%, more preferably 90%, more preferably 95%, more preferably 98%, and most preferably 99 or 100% of the dry weight of the preparation.

The invention also includes a method of improving insulin sensitivity or alleviating a symptom of insulin resistance, reducing the severity of insulin resistance, diabetes, or an associated metabolic disorder, by administering to a mammal an inhibitor of JNK expression or activity. Methods of treating or preventing the development of obesity are also within the invention. Metabolic conditions associated with insulin resistance include high blood glucose levels, markedly elevated serum insulin concentrations, and insensitivity to intravenously administered insulin. Insulin resistance is defined as the requirement of 200 or more units of insulin per day to control hyperglycemia and prevent ketosis.

Compounds are administered at a dose that is therapeutically effective. The term "therapeutically effective amount" as used herein means that the amount of a compound(s) or pharmaceutical composition elicits a beneficial biological or medicinal response in a tissue, system, animal or human. For example, a therapeutically effective amount of a JNK inhibitory compound is a dose which leads to a clinically detectable improvement in insulin sensitivity, weight loss, or a reduction in hepatic fat content.

A method of identifying an individual that is at risk of developing insulin resistance is carried out by measuring the level of JNK activity in a tissue of a mammal. Measuring the level of JNK activity in a tissue of a mammal is also useful to diagnose insulin resistance, diabetes, or a predisposition to develop the disorders. An increase in activity compared to a normal control indicates that the mammal is suffering from or is predisposed to developing insulin resistance. Insulin resistance or a predisposition thereto is also diagnosed by measuring the level of JNK expression in a tissue of a mammal. JNK expression is measured by detecting a gene product, e.g., using an antibody or other specific ligand, or by detecting gene transcription, e.g., using a standard Northern blot assay or reverse transcriptase polymerase chain reaction (RT-PCR). An increase in the level of expression compared to a normal control indicates that the mammal is suffering from or is predisposed to developing insulin resistance, or at risk of developing the disorder.

The invention also includes a method of inhibiting fat accumulation in liver tissue by contacting the tissue with an inhibitor of a JNK. For example, the JNK inhibitor reduces JNK enzymatic activity as described above, e.g., SP600125. The inhibitor preferentially reduces enzymatic activity of JNK1 compared to JNK2. For example, the inhibitor reduces JNK1 activity by at least 10%, more preferably 20%, 50%, 100%, and 200% compared to the level of reduction of JNK2 activity. The method is useful to prevent the development or slow the progression of fatty liver disease or hepatosteosis. The method is carried out by identifying an individual who is at risk of developing fatty liver disease, e.g., by identifying one who consumes excessive amounts of alcohol, one who is at least 10% above ideal body weight, one who is obese, or one who has a family history of liver disease, and administering to the individual an inhibitor of JNK1 activity. Liver tissue is contacted directly in situ, e.g., by direct injection into the liver, or systemically, e.g., by oral or intravenous administration. Contacting liver tissue with a compound which preferentially inhibits JNK1 activity leads to reduced accumulation of fat in hepatic cells.

Other features, objects, and advantages of the invention will be apparent from the description and drawings.

DESCRIPTION OF DRAWINGS

FIG. 5A is a photograph of an electrophoretic gel showing the results of a solid-phase JNK assay measuring total JNK activity. FIG. 5B is an photograph of an immunoblot showing different JNK1/2 isoforms.

FIG. 11A shows weight gain over time. FIG. 11B shows plasma glucose levels, and FIG. 11C shows plasma insulin levels. Body weight measurements and blood sampling in the ob/ob group were performed at 4 and 8 weeks of age and following a 6-h daytime food withdrawal. Statistical significance (p<0.05) is indicated by *.

FIG. 12A is a photograph of an electrophoretic gel showing JNK kinase activity. FIG. 12B is a photograph of an immunoblot showing JNK protein levels in liver, muscle and adipose tissues of lean and obese, Jnk1+/+ (wt) and Jnk1−/− mice. FIG. 12C is a bar graph showing JNK kinase activity as means±SEM of the quantitated and normalized JNK activity based on the data shown in FIGS. 12A–B. FIG. 12D is a photograph of an electrophoretic gel showing insulin receptor substrate-1 (IRS-1) phosphorylation at serine 307; total and serine 307-phosphorylated IRS-1 levels were determined in liver tissues from lean (L) and obese (O) mice. FIG. 12E is a bar graph showing the serine phosphorylation mean values. FIG. 12F is a photograph of an immunoblots of insulin-stimulated tyrosine phosphorylation (pTyr) of IR and IRS-1 in liver tissues of Jnk1−/− and Jnk1+/+ mice in specific immunoprecipitates. IR and IRS-1 tyrosine phosphorylation (pTyr) and total protein levels after vehicle (−) or insulin (+) stimulation was determined by immunoblot analyses. Each lane represents an individual mouse. FIG. 12G is a bar graph showing IR tyrosine phosphorylation mean values.

DETAILED DESCRIPTION

TNF-alpha leads to serine phosphorylation of insulin receptor substrate-1 (IRS-1) to induce insulin resistance. JNK phosphorylates IRS-1 at a serine residue. Genetic ablation of JNK was found to result in decreased body weight, increased systemic insulin sensitivity, and reduced glucose and insulin levels. Inhibitors of JNK are useful to treat obesity, insulin resistance, and diabetes. Modulation of expression or activity of JNK influences body weight, insulin resistance, and levels of insulin, glucose, and lipids in vivo.

Insulin resistant mammals, e.g., humans, include mammals suffering from non-insulin dependent diabetes mellitus (NIDDM) or pre-NIDDM and other insulin resistant states such as glucose intolerance. These conditions may be related to aging and obesity.

Inhibiting JNK kinase activity or expression of JNK is used to treat obesity and other metabolic disorders associated with disregulation of JNK and/or insulin resistance. Treatment includes the management and care of an individual for the purpose of alleviating a symptom of a disease or pathological condition. Treatment includes the administration of a compound to prevent the onset of symptoms or complications of a clinical disorder, alleviating the symptoms or complications, or eliminating the disease, condition, or disorder. Treating an insulin resistant mammal includes increasing insulin sensitivity and/or insulin secretion to prevent islet cell failure.

JNK inhibition is also useful to alleviate the symptoms of other conditions associated with insulin resistance such as cancer cachexia, HIV-1 infection, polycystic ovarian syndrome, atherosclerosis, and severe burns. In the latter case, acute phase burn victims are given a JNK inhibitor shortly after the burn incident to prevent or decrease the development of insulin resistance.

Improvement of Conditions Related to Obesity and Insulin Resistance

Figure 1:
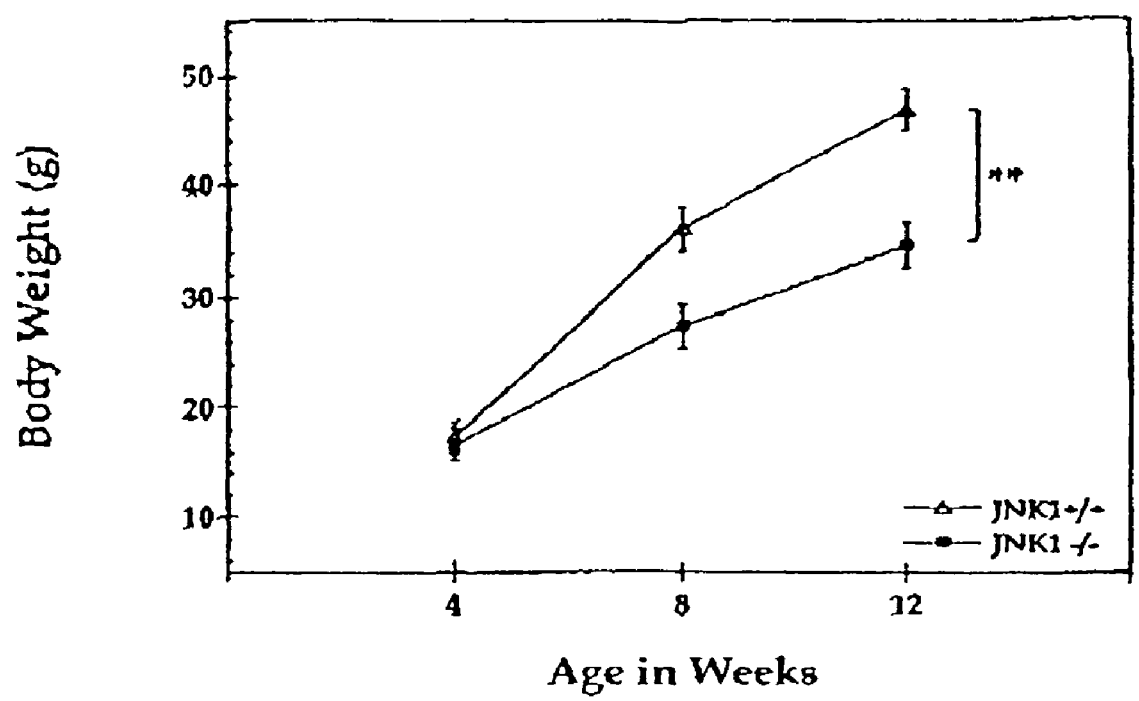
FIG. 1 is a line graph showing body weight in JNK-deficient (JNK −/−) mice compared to wild type (JNK +/+) control mice. JNK-deficient and control mice were put on a high fat diet for 12 weeks. The body weight was of JNK-deficient mice was consistently and significantly reduced compared to control mice fed the same diet.
Figure 2A:
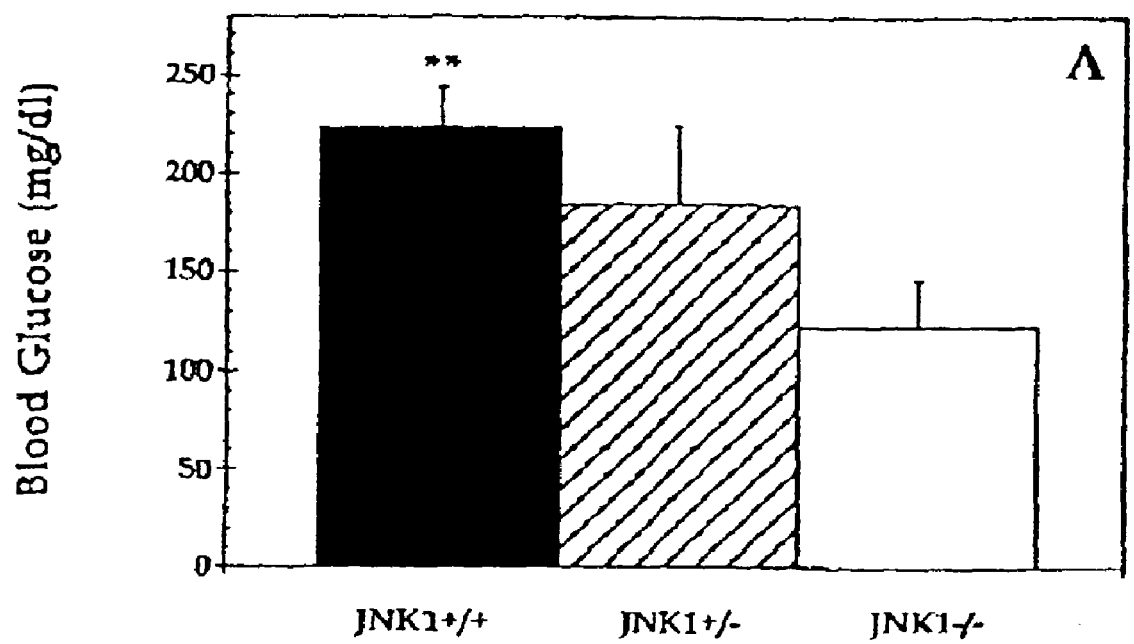
FIG. 2A is a bar graph showing blood glucose levels in JNK-deficient mice compared to control mice. Both groups of mice were fed a high fat diet for 12 weeks. Blood glucose levels of JNK-deficient mice were significantly reduced compared to wild type mice.
Figure 2B:
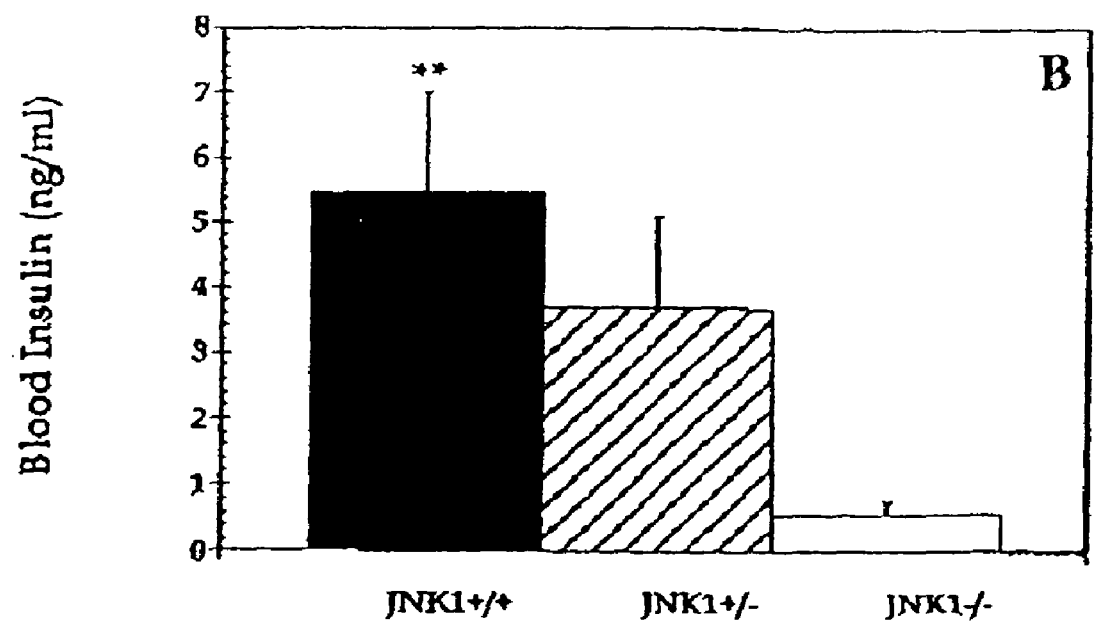
FIG. 2B is a bar graph showing blood insulin levels in JNK-deficient mice compared to control mice. Both groups of mice were fed a high fat diet for 12 weeks. Blood insulin levels of JNK-deficient mice were significantly reduced compared to wild type mice. The reduction in blood glucose and blood insulin levels shown in FIGS. 2A–B indicate improved insulin sensivity in JNK-deficient mice compared to control mice.
Figure 3A:
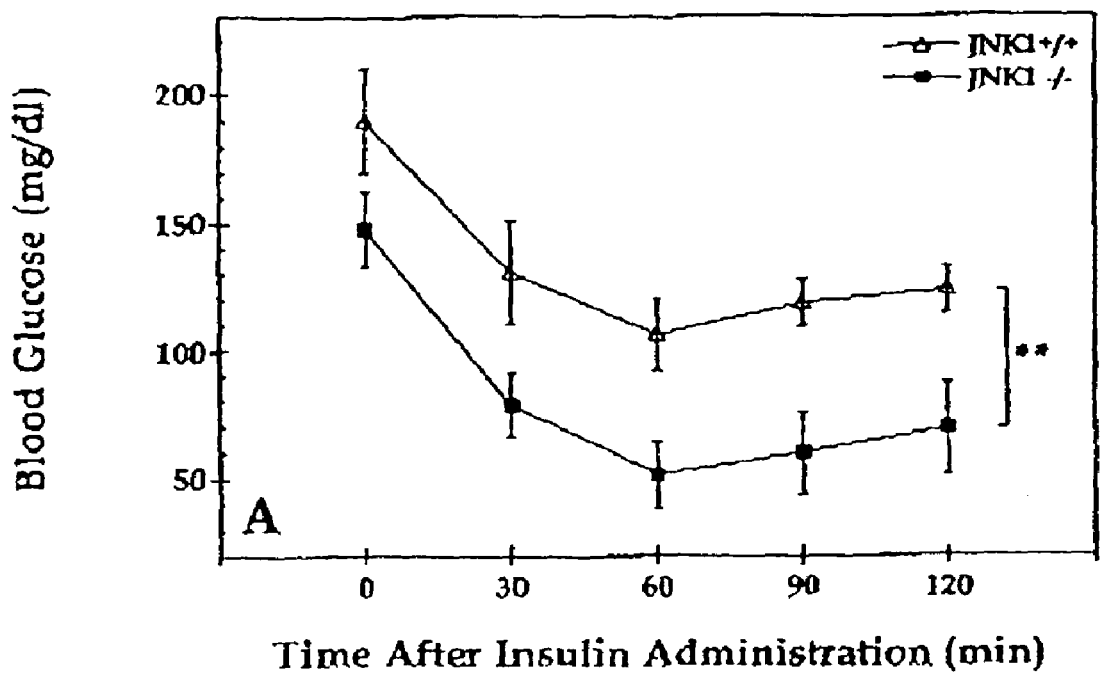
FIG. 3A is a line graph showing the results of an insulin tolerance test in JNK-deficient and control mice. Both groups of mice were fed a high fat diet for 12 weeks. At t=0, animals were injected with insulin. Blood levels of glucose and insulin were monitored every 30 minutes.
Figure 3B:
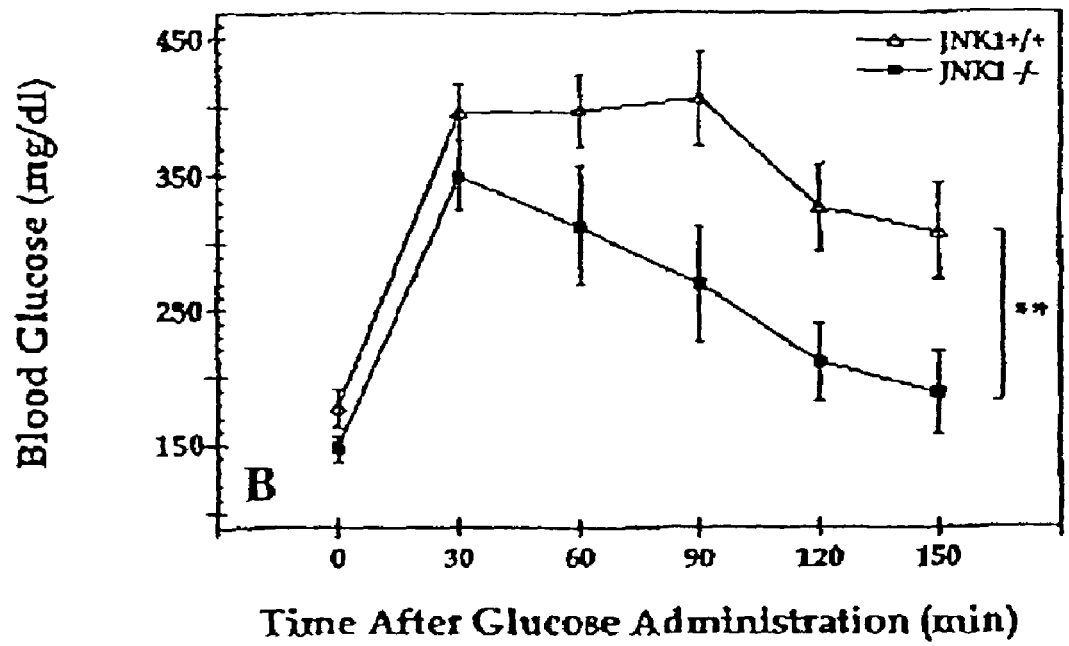
FIG. 3B is a line graph showing the results of a glucose tolerance test in JNK-deficient and control mice. Both groups of mice were fed a high fat diet for 12 weeks. At t=0, animals were injected with insulin. Blood levels of glucose and insulin were monitored every 30 minutes. The data shown in FIGS. 3A–3B indicate that a reduction in JNK is correlated with improved insulin action.

JNK-deficient mice were generated using methods known in the art. The mice contain a null mutation in a gene encoding a JNK, and therefore, fail to express the corresponding gene product or express a non-functional gene product. FIG. 1 shows that JNK-deficient mice fed a high fat diet weigh less than wild type control mice fed the same diet. FIGS. 2A–B and FIGS. 3A–B indicate that JNK-deficient mice demonstrated improved insulin sensitivity compared to wild type control mice. In most tissues, inhibition of one isotype of JNK leads to an increase in expression of another isotype. However, in certain tissues, e.g., liver, white adipose tissue, and muscle, JNK2 did not compensate for a decrease or loss of JNK-1 expression or activity. Taken together, these data indicate that contacting cells or a tissue of a mammal with an inhibitor of JNK expression or an inhibitor of JNK enzyme activity improves insulin sensitivity. The data also indicate that such compounds are useful to treat or prevent the development of obesity.

Therapeutic Administration

Mammals such a humans, which are overweight, obese, or at risk of becoming so, can be treated with compounds which decrease JNK expression or activity. In addition, humans, who are at risk of developing hepatosteosis, also benefit by intervention to reduce JNK expression or activity. By "activity" is meant kinase enzyme activity.

Methods of determining whether or not an individual is overweight or obese are known in the art. For example, Body mass index (BMI) is measured ($kg/m^2$ (or $lb/in^2 \times 704.5$)). Alternatively, waist circumference (estimates fat distribution), waist-to-hip ratio (estimates fat distribution), skinfold thickness (if measured at several sites, estimates fat distribution), or bioimpedance (based on principle that lean mass conducts current better than fat mass (i.e. fat mass impedes current), estimates % fat) is measured. The parameters for normal, overweight, or obese individuals is as follows: Underweight: BMI <18.5; Normal: BMI 18.5 to 24.9; Overweight: BMI=25 to 29.9. Overweight individuals are characterized as having a waist circumference of >94 cm for men or >80 cm for women and waist to hip ratios of ≧0.95 in men and ≧0.80 in women. Obese individuals are characterized as having a BMI of 30 to 34.9, being greater than 20% above "normal" weight for height, having a body fat percentage >30% for women and 25% for men, and having a waist circumference >102 cm (40 inches) for men or 88 cm (35 inches) for women. Individuals with severe or morbid obesity are characterized as having a BMI of ≧35.

Individuals who are at risk of developing hepatosteosis include overweight persons as well as those who consume excessive amounts of alcohol, e.g., greater than two drinks per day for females, and greater than 3 drinks per day for males. Candidates for JNK inhibitory treatment are also identified by examining the liver by ultrasonography to detect hepatomegaly or excessive fat accumulation or by biopsy to detect fat deposits. Administration of a JNK inhibitory compound protects agains the development of hepatosteosis and/or slows its progression. The inhibitor can be administered locally or systemically as described below.

Inhibitors of JNK kinase activity are known in the art, e.g., SP-600125 (Signal Pharmaceuticals Inc., San Diego, Calif.). SP-600125 is a selective JNK inhibitor, which inhibits the phosphorylation of c-Jun in a dose-dependent manner. This inhibitor is selective for JNK compared to other kinases and other enzymes. Other compounds, which inhibit JNK activity, include genistein, herbimycin A, 4-amino-5-(4-chlorophenol)-7-(t-butyl)pyrazolo[3,4-D]pyrimidine (or PP2). EGFR specific inhibitor, tyrphostin AG1478 also inhibits c-JNK activation.

Expression of JNK is inhibited by inducing expression of an endogenous JNK inhibitor, e.g., Hsp72 (Park et al, 2001, EMBO J. 20:446–56). Cell-permeable peptide inhibitors of JNK (Bonny et al., 2001, Diabetes 50:77–82). Inhibition of JNK may be accomplished by inducing expression of JNK interacting protein (JIP-1), e.g., by inducing overexpression of the JNK binding domain of JIP-1.

A peptide inhibitor includes amino acids 33–79 of c-Jun (U.S. Pat. No. 6,193,965). This peptide is a competitive inhibitor, which decreases the amount of c-Jun activation by JNK. Antibodies or other ligands, which bind to an ATP binding site or catalytic domain of JNK are used to inhibit JNK kinase activity. The amino acid sequence, nucleotide sequence, and domains of JNK1 are described in U.S. Pat. No. 6,193,965.

Inhibitory compounds can be formulated with conventional excipients, i.e., pharmaceutically acceptable organic or inorganic carrier substances suitable for parenteral, enteral (e.g., oral or inhalation) or topical application. Suitable pharmaceutically acceptable carriers include but are not limited to water, salt solutions, alcohols, gum arabic, vegetable oils, benzyl alcohols, polyethylene glycols ,gelatin, carbohydrates such as lactose, amylose or starch, magnesium stearate, talc, viscous paraffin, perfume oil, fatty acid esters, hydroxy methylcellulose, polyvinyl pyrrolidone, etc. Compounds are administered using conventional methods. For parenteral application, inhibitors are in the form of injectable, sterile solutions, e.g., oily or aqueous solutions, as well as suspensions, emulsions, or implants. Other formulations suitable for parenteral adminstration include tablets, liquids, drops, suppositories, or capsules. Sustained or directed release compositions can be formulated, e.g., liposomes or those wherein the active component is protected with differentially degradable coatings, e.g., by microencapsulation, multiple coatings, etc. Administration by injection, e.g. subcutaneous, intramuscular or constant infusion by intravenous drip is also useful. The compounds are also administered by transdermally, e.g., by transdermal patch, to allow administration over a long period of time, e.g., over days or weeks. The compounds are at doses of 50 to about 150 µg/kg in a pharmaceutically acceptable carrier per unit dosage. Doses are adjusted depending upon the response of the mammal to the drug.

Diagnosis of Pathological Conditions

Figure 4:
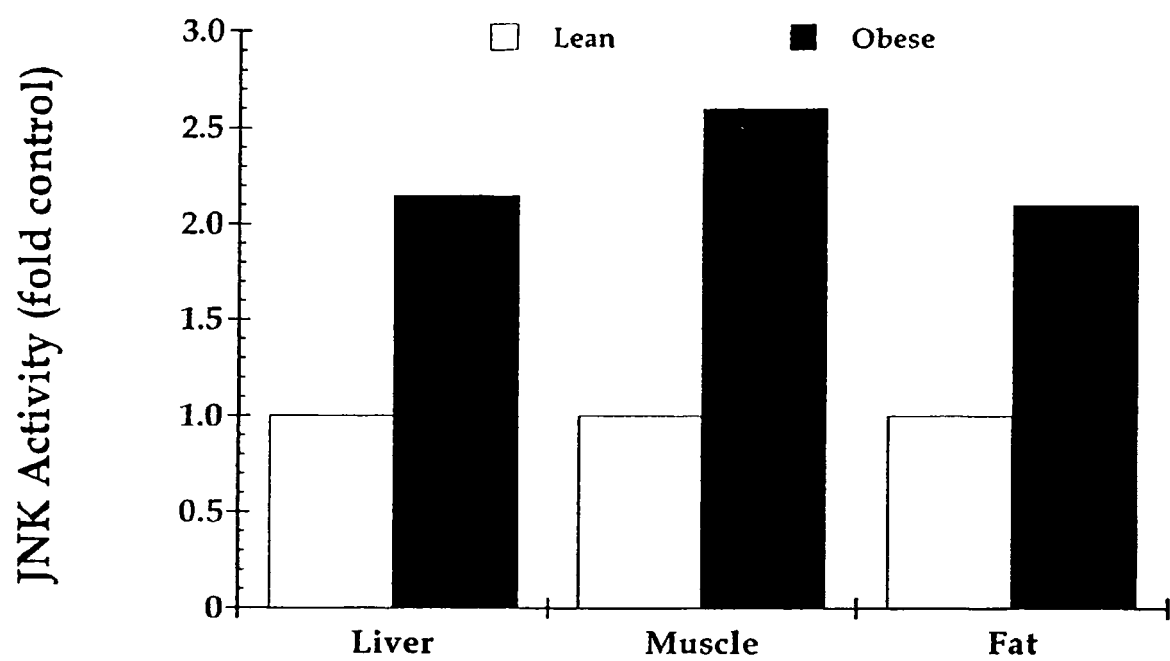
FIG. 4 is a bar graph showing increased JNK activity in obesity.

Patients suffering from or at risk of developing a pathological condition such as aberrant glucose metabolism can be identified by measuring JNK activity and/or proteins level. FIG. 4 shows increased JNK activity in tissues derived from obese individuals compared to non-obese individuals. An increase in JNK enzyme activity, e.g., JNK1, in bodily tissues or fluids indicates a diagnosis of insulin resistance, diabetes, or a predisposition thereto. An increase also indicates a predisposition to obesity.

Diagnostic assays can be carried out by obtaining a tissue sample or sample of bodily fluid from an individual and measuring JNK activity using a standard kinase assay. For example, the data in FIG. 4 was generated using a standard solid phase kinase assay. The assay was carried out by contacting tissue or a cell suspension (e.g., 600 µg tissue) with 20 µl of glutathione S-transferase (GST)-agarose resin suspension to which 5 µg of GST-c-Jun (amino acids 1–79) is bound. The mixture was agitated at 4° C. overnight, pelleted by centrifugation, and washed in a buffer containing 10 mM HEPES pH 7.7, 50 mM NaCl, 2.5 mM $MgCl_2$. The pelleted beads were subjected to an in vitro kinase assay described by Hibi et al. Upon staining with Coomassie Blue R250 and autoradiography, the bands corresponding to GST-c-Jun were quantified by PhosphorImager. This assay measures total JNK enzyme activity.

An increase in JNK activity of at least 10% compared to a normal control indicates a diagnosis of diabetes, insulin resistance, or a risk of developing diabetes, insulin resistance, or obesity. A greater increase over a normal level (e.g., 20%, 25%, 30%, 40%, or 50%) indicates a greater risk of developing a disorder or greater severity of disease. Preferably, the increase in activity is at least 2-fold that of a normal control value.

To determine the kinase activity of JNK1 (independent of other JNK isotypes such as JNK1 or JNK2), a tissue sample can be obtained from a test subject. Cells can be lysed, and proteins extracted from the tissue sample. The membrane fraction can be removed by centrifugation. The supernatant can be subjected to immunoprecipitation using a JNK1 specific antibody. JNK1 specific antibodies are known in the art and commercially available (e.g., MAb 333.8 from Pharmingen, Inc., La Jolla, Calif.). Following immunoprecipitation of JNK1, a standard kinase assay can be performed as described above. A preferential increase in JNK1 (relative to other JNK isotypes) compared to a normal control JNK1 value indicates a diagnosis of diabetes, insulin resistance, or predisposition to develop diabetes, insulin resistance, or obesity.

Fatty liver disease or a risk of developing the disease is carried out by measuring the level of JNK1 expression or activity in a liver tissue sample. The tissue sample is obtained by biopsy. An increase in the amount of JNK1 expression (e.g., measured by detecting JNK protein or by detecting JNK gene transcripts) indicates that the individual from which the tissue was obtained is suffering from or at risk of developing a condition of excessive fat accumulation in the liver.

Identification of JNK Inhibitors

Inhibitors of JNK enzymatic activity are identified by contacting a JNK with a candidate compound. A control assay is run in parallel; the control assay includes a JNK in the absence of the candidate compound. Kinase activity is measured using methods known in the art (e.g., as described by Hibi et al., 1993, Genes Dev. 7:2135–2148). A decrease in enzyme activity in the presence of the compound compared to the level in the absence of the compound indicates that the compound is a JNK inhibitor.

In addition to a standard solid phase kinase assay, an in-gel kinase assay may be used. The in-gel assay is carried out using known methods, e.g., as described by Kameshita and Fujisawa, Anal. Biochem., 1989, Anal. Biochem. 183: 139–143. c-Jun binding proteins were isolated from whole cell extracts by using GSH-agarose beads containing GST-c-Jun. Proteins are eluted in a standard SDS-PAGE sample buffer and resolved on 10% SDS-polyacrylamide gel, which was polymerized in the absence or presence of GST-c-Jun. After electrophoresis, the gel was washed and incubated in 200 ml of 6M urea. After incubation in a buffer containing 0.05% Tween 20 and either 3M, 1.5M or 0.75M urea, the gel was washed and incubated with kinase buffer containing $^{32}$P-ATP. After the reaction, the gel was washed with 100 ml of 5% tricholoroacetic acid and 1% sodium pyrophosphate at room temperature several times, followed by drying and autoradiography.

Inhibitors of JNK expression are identified by incubating a JNK promoter region operably linked to a reporter sequence with a candidate compound. An decrease in transcription of the reporter gene (or an increase in the amount of the reporter gene product) in the presence of the candidate compound compared to the level in the absence of the compound indicates that the compound decreases JNK expression.

JNK1 Plays a Central Role in Obesity and Insulin Resistance

Obesity and type 2 diabetes are associated with a state of chronically enhanced inflammatory response characterized by abnormal cytokine production, increased circulating acute-phase reactants and other stress-induced molecules. Many of these alterations seem to be initiated and reside within adipose tissue, an unusual site for inflammatory responses. Elevated production of TNF-α by adipose tissue was found in a variety of experimental obesity models and in obese humans, and free fatty acids (FFAs), are also implicated in the etiology of obesity-induced insulin resistance. Since both TNF-α and FFAs are potent JNK activators, experiments were carried out to determine whether obesity is associated with alterations in stress-activated and inflammatory responses through in this signaling pathway and whether JNKs are causally linked to aberrant metabolic control in this state.

Mice deficient in JNK1 and JNK2 were made using known methods (e.g., Davis et al. 2000, Cell 103:239–252).

In the studies described herein, Jnk1−/− mice on C57BL/6/129 mixed genetic background were backcrossed for 3 generations to C57BL/6 prior to experiments. These mice were intercrossed with Jnk2−/−mice on C57BL/6 background to produce mice heterozygous for mutations in both JNK1 and JNK2. All mice were generated from intercrosses between these double heterozygotes and groups were derived from littermates. ob/ob-Jnk1+/+ and ob/ob-Jnk1−/− mice were generated by intercrossing Jnk1−/− and OB/ob animals to generate double heterozygotes and with subsequent crosses with OB/ob breeders to create double homozygous mutant mice.

Diet study and metabolic measurements were carried out as follows. Male mice of different genotypes were housed in a barrier free facility and placed on a high fat/high carbohydrate diet ad libitum (Diet F3282, Bioserve, N.J.) at 4 weeks of age and were followed for a period of twelve weeks. Parallel groups were left on standard rodent chow to serve as controls. Total body weight measurements were initiated at 4-week of age. Blood samples were collected after a 6-hour, daytime fast at indicated ages and biochemical measures were conducted using 12-week-old animals. Standard glucose and insulin tolerance tests were performed on conscious mice following a 6 hour fast.

Total JNK Enzymatic Activity and Total JNK Protein Levels

JNK activity was measured in liver, muscle and adipose tissues of various models of obesity compared to the lean controls to determine whether obesity activates this pathway. Measurement of JNK activity and protein levels were carried out as follows. Tissue extracts (600 μg protein) were mixed with 20 μl of glutathione S-transferase (GST)-agarose resin suspension (Sigma) to which 5 μg of GST-c-Jun1–79 were bound. The mixture was agitated at 40° C. for overnight, pelleted by centrifugation, washed twice and JNK activity was measured using known methods, e.g., as described by Yuan et al., 2001, Immunity 14:217–230. Upon staining with Commassie Brilliant Blue R250 and autoradiography, the bands corresponding to GST-c-Jun were quantified by Molecular Dynamics PhosphorImager.

Figure 5C:
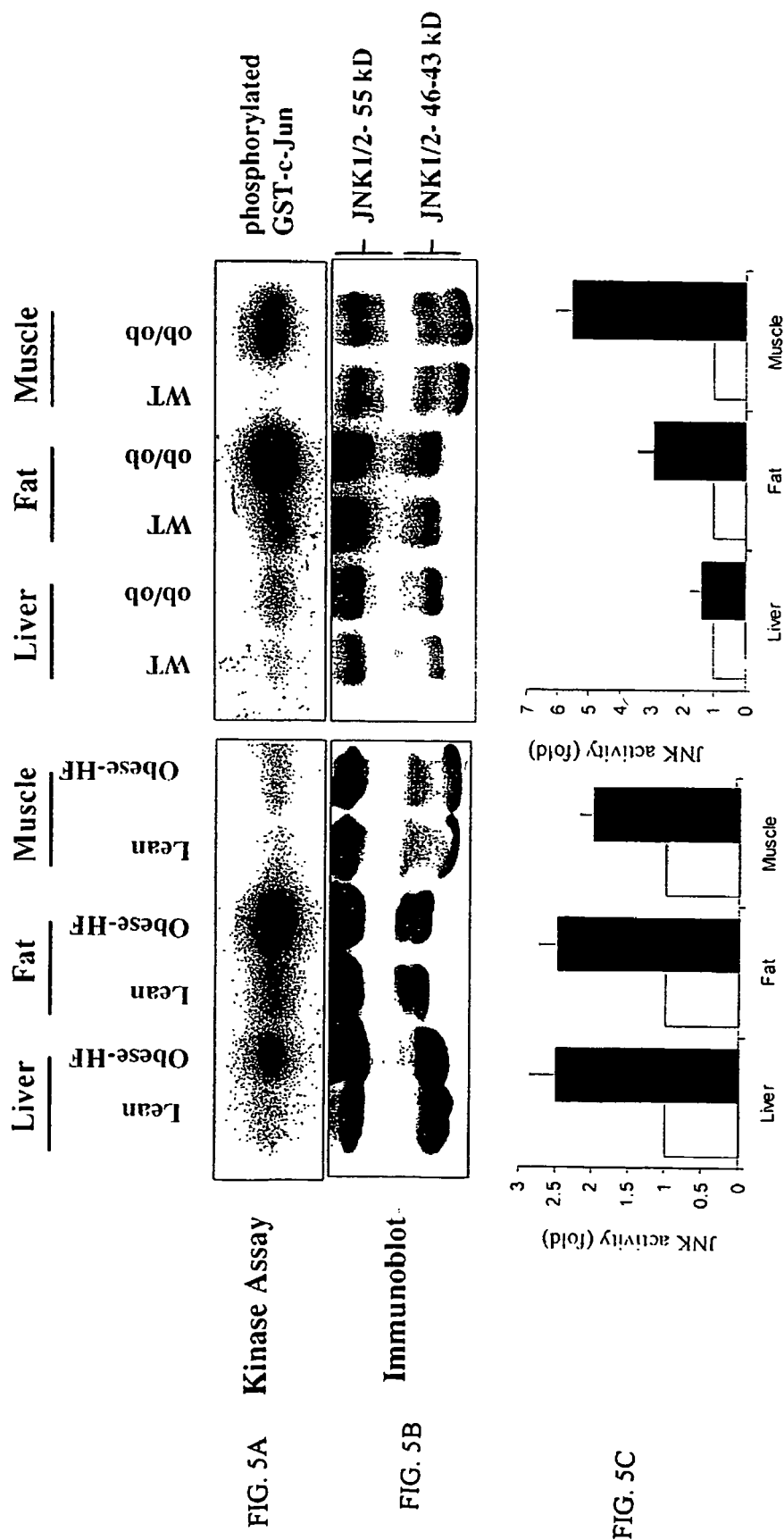
FIG. 5C is a bar graph showing means ±SEM of the quantitated and normalized activity. All mice assayed were male, 16-week-old and on C57B1/6 background. Total JNK activity and protein levels was measured in liver, muscle and adipose tissues of lean and obese [dietary (obese-HF) and genetic (ob/ob)] mice.

In both dietary and genetic (ob/ob) models of obesity, there was a significant increase in total JNK activity in all of the tissues tested (FIGS. 5A–C.). In these tissues, there was no difference in the level of either JNK1 or JNK2 proteins, suggesting that the activity of one or both of these kinases is increased in response to obesity.

Diet-induced Obesity is Inhibited by Reduction in JNK Level

Figure 6B:
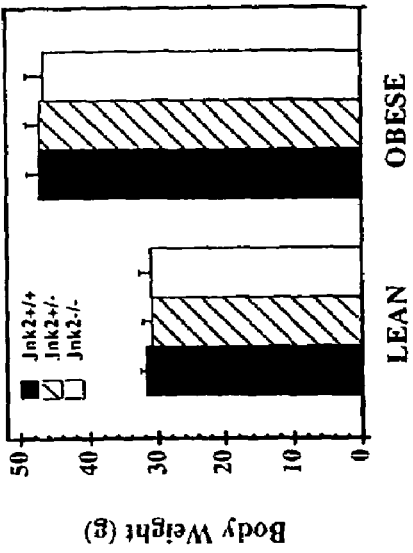
FIGS. 6B and 6D are bar graphs representing means ±SEM of body weights of male mice at 16 weeks of age. Development of diet-induced obesity was measrued in the Jnk2−/− (FIGS. 6A and 6B) and Jnk1−/− (FIGS. 6C and 6D) mice. All data are collected from male mice (n=10 in each group). Statistical significance (p<0.05) in two-tailed Student t test comparing Jnk1−/− or Jnk2−/− mice with controls is indicated by *.
Figure 6D:
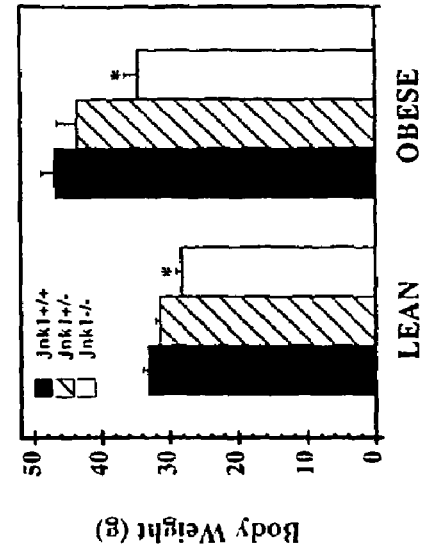
Figure 6A:
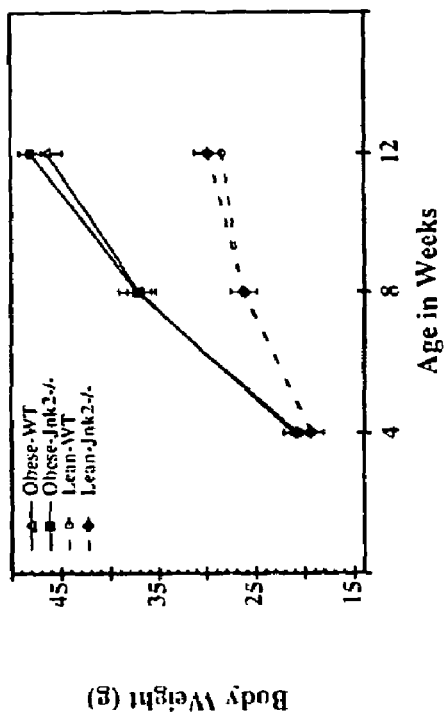
FIGS. 6A and 6C are line graphs showing weight gain over time.
Figure 6C:
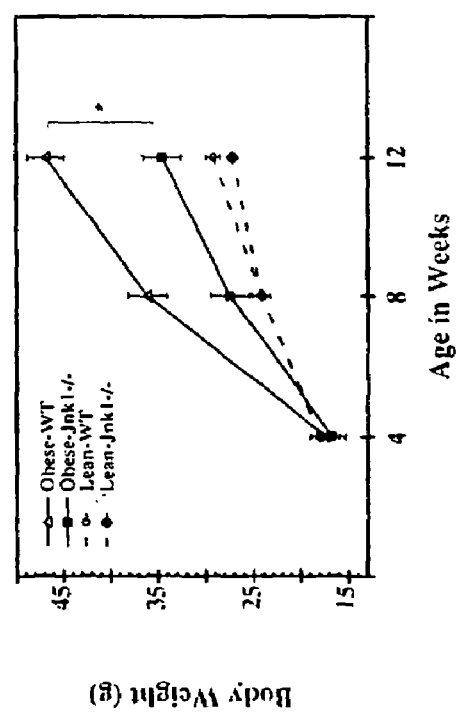

JNK activity was further evaluated to test the functional significance of the observed increase in the pathogenesis of obesity, insulin resistance and type 2 diabetes. To address this question, obesity was induced in mice lacking either JNK1 (Jnk1−/−) or JNK2 (Jnk2−/−). Jnk1−/− or Jnk2−/− mice and their control littermates (Jnk1+/+ or Jnk1+/− and Jnk2+/+ or Jnk2+/−) were placed on a high fat (50% of total calories derived from fat) and high caloric diet (5286 kcal/kg, Bioserve, N.J.) along with a control group in each genotype on standard diet. On high fat diet, both controls and Jnk2−/− mice developed marked obesity as compared to mice kept on standard diet (FIGS. 6A and 6B). The weight gain curves of these animals were indistinguishable on either standard or high fat diet. However, weight gain on both standard and high fat diets was significantly reduced for the Jnk1−/− group (FIGS. 6C and 6D). Animals with one targeted allele of Jnk1 (Jnk1+/−) displayed intermediary body weight between wild type and Jnk1−/− mice maintained on either diet (FIG. 6D).

Inhibition of JNK1 Activity and Reduced Adipocity

Figure 7C:
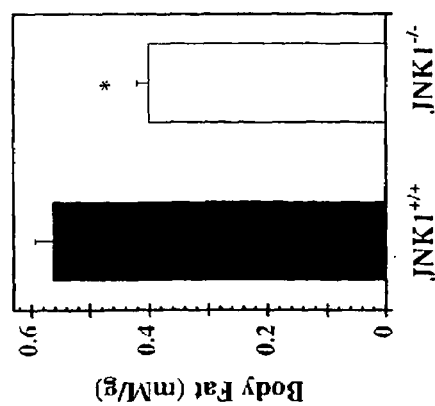
FIGS. 7A–H are a series of bar graphs showing the results of analyses of adipose tissue morphology and adiposity in Jnk1−/− mice and wild type controls. Histological sections of epididymal fat pads (FIG. 7A) and epididymal and subcutaneous fat pad weights (FIG. 7B) of 16-week old male Jnk1−/− and Jnk1+/+ mice (n=3 in FIGS. 7A and 9 in FIG. 7B). Total body composition (FIG. 7C), fecal lipid content (FIG. 7D), daily food intake (FIG. 7E), core body temperature (FIG. 7F) and serum adiponectin (FIG. 7G) and resistin (FIG. 7H) levels of Jnk1−/− and Jnk1+/+ mice. Total carcass lipid analysis was performed to determine fat mass of individual mice (n=6 in each group). Food intake was studied in 12 week-old male mice on high fat diet (n=9 in Jnk1+/+ and n=6 in Jnk1−/−). Fecal lipid content and core body temperature were measured in the same group of mice in FIG. 7C. Statistical significance (p<0.05) in two-tailed Student t test comparing Jnk1+/+ or Jnk1−/− mice is indicated by *.
Figure 7B:
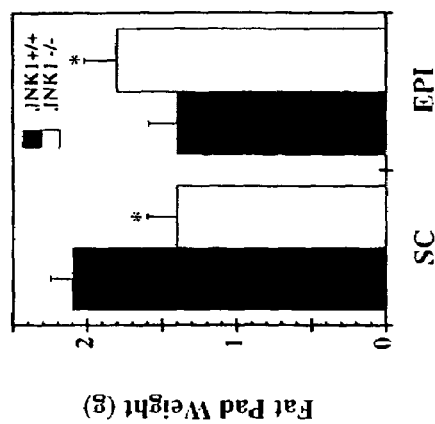
Figure 7F:
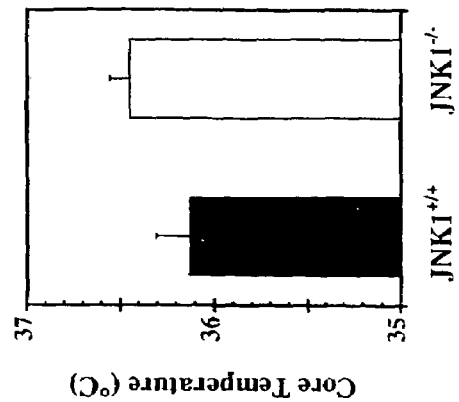
Figure 7E:
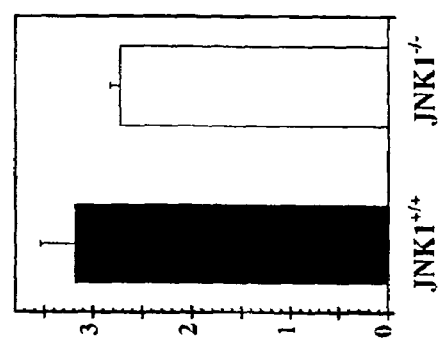
Figure 7A:
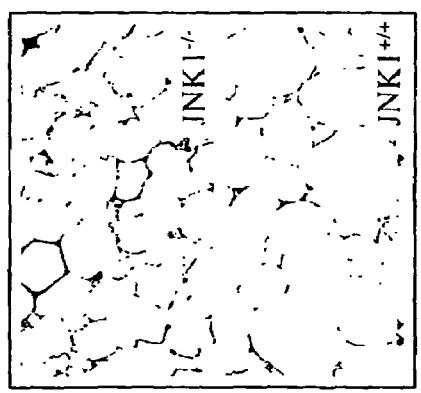

Studies were carried out to determine whether the differences in weight gain are related to alterations in adiposity. Adipose tissue sections obtained from Jnk1−/− mice exhibited reduced adipocyte size relative to wild type controls (FIG. 7A). This reductionwas not observed in Jnk2−/− adipose tissue. The fat pad weights of Jnk1+/+, Jnk1+/− and Jnk1−/− mice were similar in the lean group at both subcutaneous and epididymal fat depots. However, in the obese group, the average weight of the subcutaneous fat depot was reduced by 33% in Jnk1−/− mice compared to the wild type controls (FIG. 7B). Surprisingly, the weight of the epididymal fat pad was even higher in the obese Jnk1−/− group compared to the wild type (FIG. 7B). No difference in fat pad weight was evident between Jnk2−/− and wild type mice in either condition. To investigate systemic alterations in adiposity, total body composition was examined. These studies demonstrated significantly reduced total body adiposity in Jnk1−/− mice compared to controls (FIG. 7C). In contrast, body composition of Jnk2−/− group was indistinguishable from wild type controls.

Figure 7D:
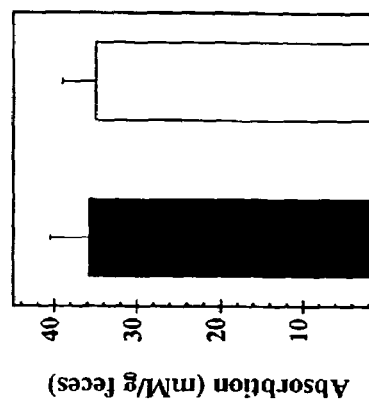

To address alternative causes for reduced body weight in Jnk1−/− mice, lipid metabolism, food intake, intestinal lipid absorption and core body temperature of Jnk1−/− and Jnk1+/+ mice were compared. No significant difference was observed in plasma triglyceride, cholesterol and FFA levels between genotypes. Examination of fecal lipid content also did not reveal any differences between genotypes, thus, excluding changes in intestinal lipid absorption (FIG. 7D). There was a very small decrease in daily food intake (0.46 g/day) in obese Jnk1−/− mice compared to wild type, but this difference did not approach statistical significance (FIG. 7E). There was also a small increase (0.32° C.) in core body temperature in obese Jnk1−/− mice, which was also statistically insignificant (FIG. 7F). The results indicate that the JNK1-deficiency leads to decreased adipocyte size and reduced adiposity and adipose redistribution in the context of dietary obesity without other metabolic abnormalities. These results also indicate that Jnk1−/− mice metabolize lipids more efficiently than wild type animals.

Figure 7H:
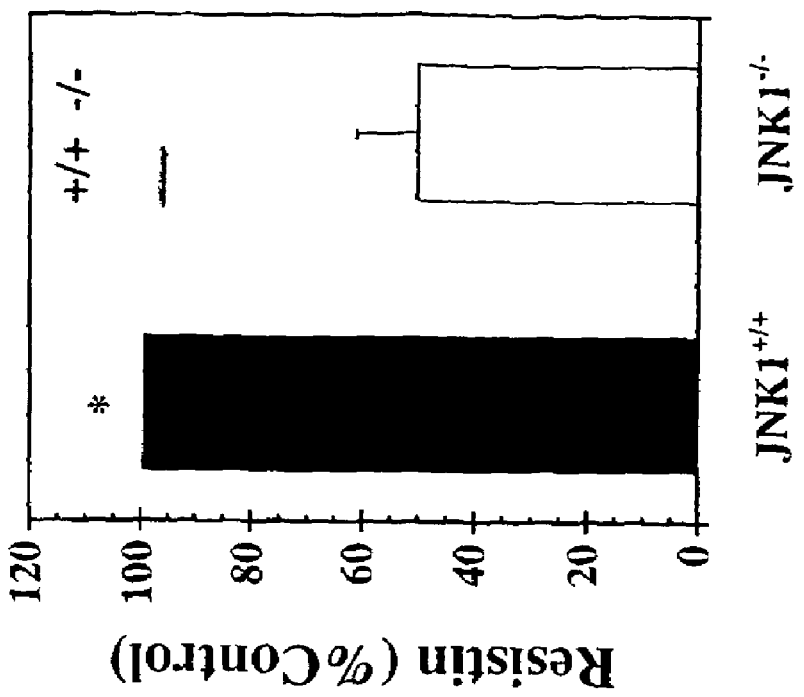
Figure 7G:
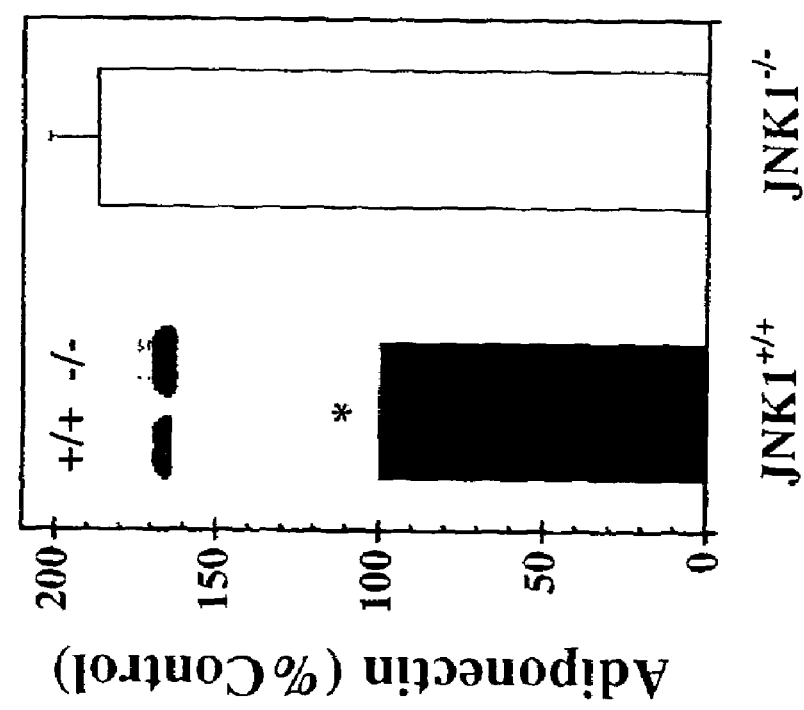

Adipose tissue can have a substantial impact on systemic glucose homeostasis through the production of various bioactive molecules. Serum levels of adipocyte-derived secreted proteins were examined to evaluate their roles in obesity and insulin action. ACRP30/Adiponectin levels in the obese Jnk1−/− mice were found to be significantly higher compared to obese Jnk1+/+ controls (FIG. 7G). In contrast, the levels of resistin protein were lower in Jnk1−/− mice compared to Jnk1+/+ animals (FIG. 7H). Adiponectin has been shown to act as a mediator of fatty acid oxidation and hepatic insulin sensitivity, and resistin may have a role in insulin resistance. The alterations in adiponectin and resistin could also impact systemic insulin sensitivity.

Figure 8A:
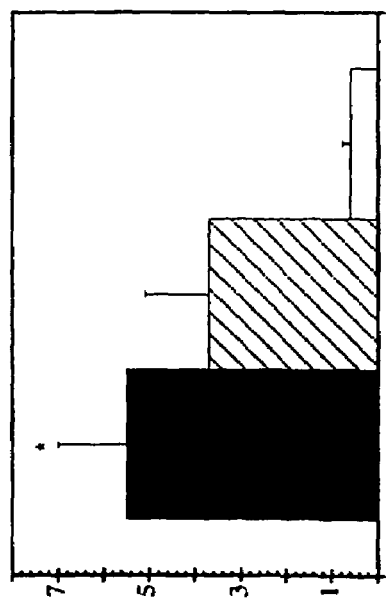
FIGS. 8A and 8C are bar graphs showing blood glucose levels (a measure of glucose homeostasis) by fasting plasma glucose.
Figure 8B:
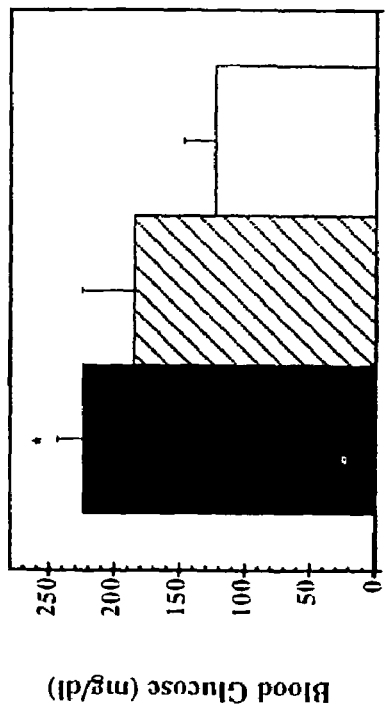
FIGS. 8B and 8D are bar graphs showing blood insulin levels.
Figure 8C:
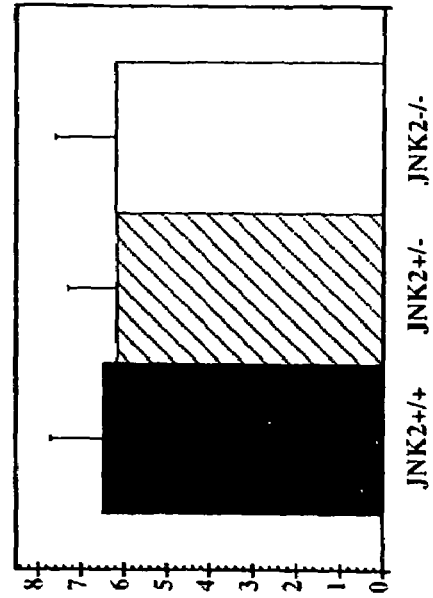
Figure 8D:
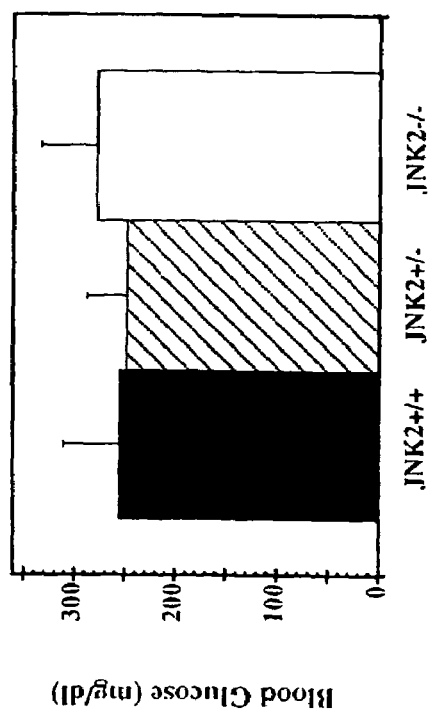

Inhibition of JNK1 Protects Against Development of Obesity-induced Insulin Resistance To test the role of JNK in insulin sensitivity, glucose homeostasis in Jnk1−/− and Jnk2−/− mice was evaluated and compared to wild type controls. Measurement of fasting blood glucose levels demonstrated that obese Jnk1+/+ mice developed mild hyperglycemia compared to lean wild type controls (224±20 vs. 126±11 mg/dl, P<0.001). In contrast, obese Jnk1−/− mice had significantly lower blood glucose compared to obese Jnk1+/+ mice (FIG. 8A). At 12 weeks of age, the blood glucose in obese Jnk1−/− mice was indistinguishable from that of lean Jnk1+/+ or Jnk1−/− animals (148±15 vs. 126±11 and 127±8 mg/dl, mean±SEM, p=0.8). Obese wild type mice also developed significant fasting hyperinsulinemia compared to those on standard diet (5.5±1.5 vs. 0.69 ng/ml P<0.001). Blood insulin levels in obese Jnk1−/− mice were significantly lower compared to obese Jnk1+/+ animals (FIG. 8B) and indistinguishable from either Jnk1+/+ or Jnk1−/− lean mice (0.63±0.18 vs. 0.69±0.16 and 0.57±0.13 ng/ml, p=0.8). Blood glucose and insulin levels in Jnk1+/− mice were intermediate between those of Jnk1+/+ and Jnk1−/− animals but these differences were statistically insignificant (FIGS. 8A and 8B). Obese Jnk2−/− mice developed a similar degree of hyperglycemia and hyperinsulinemia as obese wild type animals. Blood glucose and insulin levels were indistinguishable between the Jnk2−/−, Jnk2+/− and Jnk2+/+ groups (FIGS. 8C and 8D). The rise in blood glucose and insulin in animals on high fat diet indicates obesity-induced insulin resistance and progression to type 2 diabetes. The data indicate that the JNK1- but not JNK2-deficient animals are protected from development of obesity-induced insulin resistance.

Figure 8E:
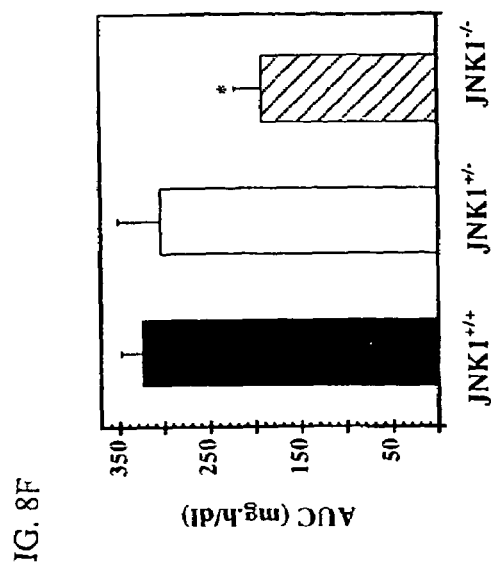
FIGS. 8E/I are line graphs and FIGS. 8F/J are bar graphs showing the results of insulin tolerance tests in lean and obese Jnk1−/−, Jnk2−/− and control male mice at 16-weeks of age.
Figure 8F:
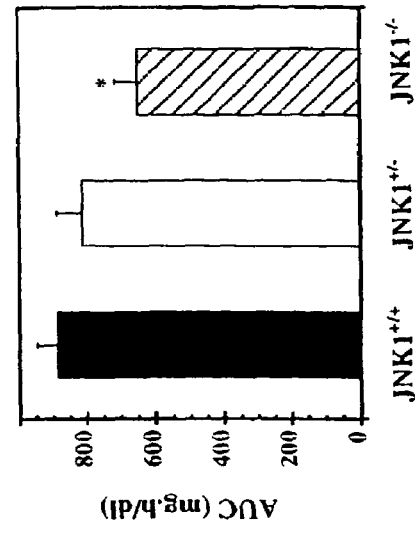
In FIGS. 8F, 8H, 8J, and 8L, "AUC" designates the area under curve for the glucose disposal curves in FIGS. 8F, 8H, 8J and 8L. Investigation of the dynamics of the responses to the tolerance tests were done by ANOVA repeated measures analysis (Statview 4.01, Abacus Concepts, Berkeley, Calif.) and demonstrated statistically significant differences between Jnk1−/− and Jnk1+/+ mice indicated by * (p<0.001).
Figure 8G:
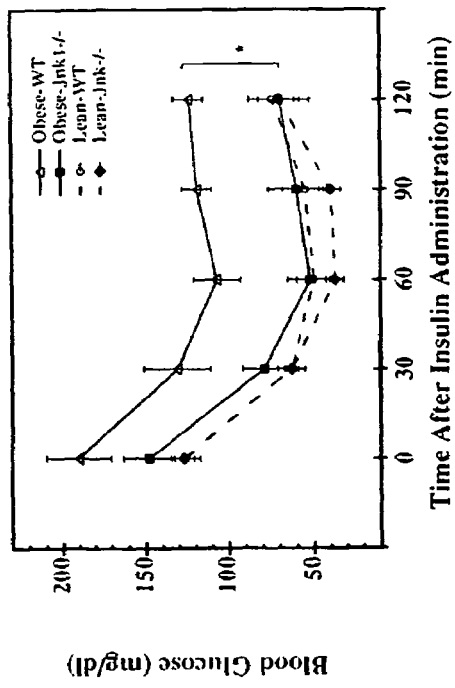
FIGS. 8G/K are line graphs and FIGS. 8H/L are bar graphs showing the results of glucose toleranc tests in lean and obese Jnk1−/−, Jnk2−/− and control male mice at 16-weeks of age.
Figure 8H:
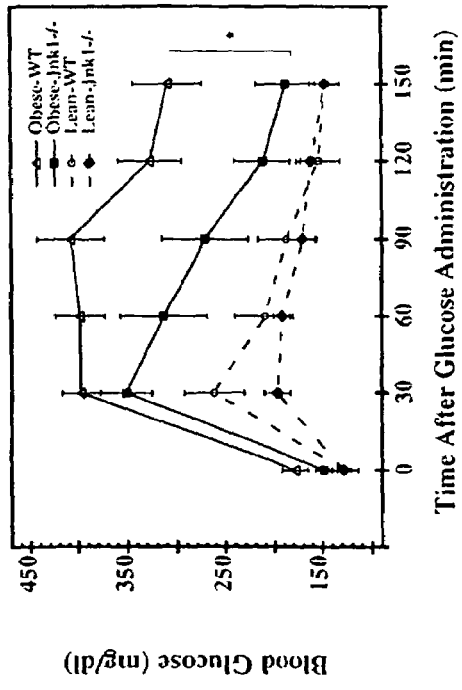
Figure 8J:
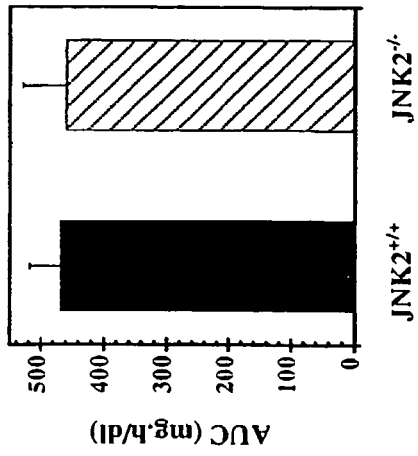
Figure 8L:
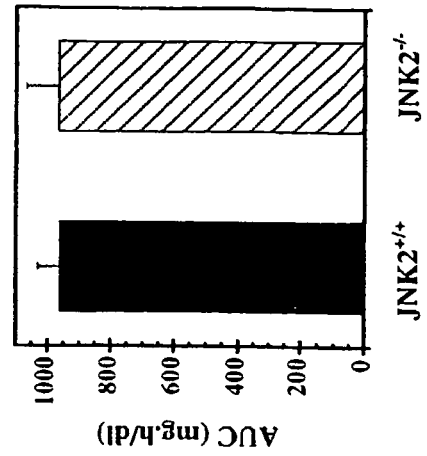
Figure 8I:
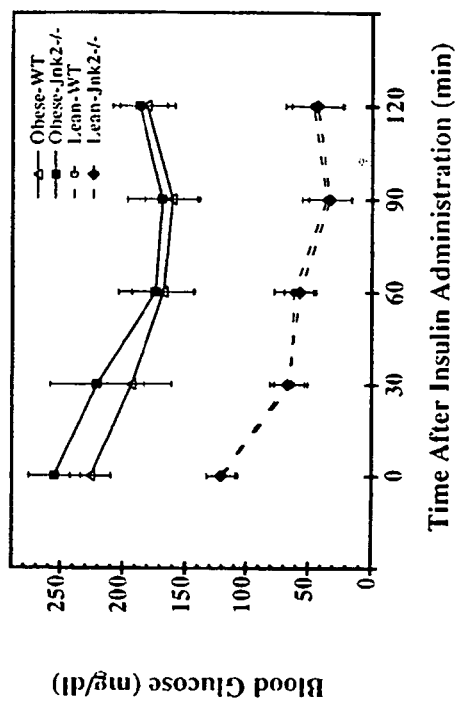
Figure 8K:
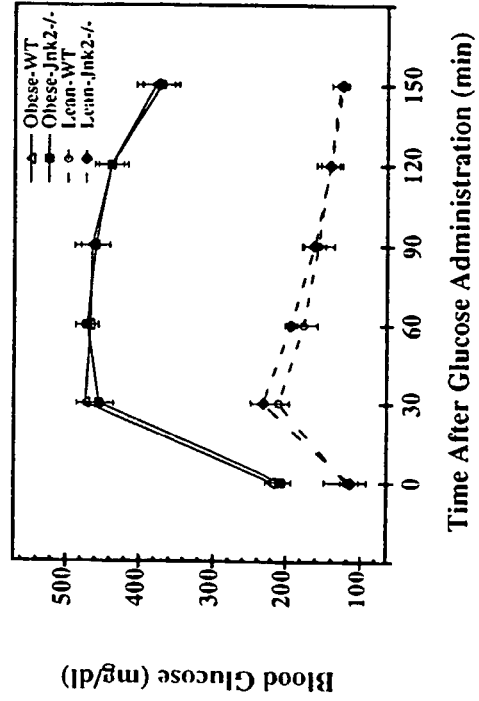

To further investigate this point, intraperitoneal insulin (IITT) and glucose (IGTT) tolerance tests were performed. The hypoglycemic response to insulin was lower in obese Jnk1+/+ mice throughout the experiment than in obese Jnk1−/− animals (FIG. 8E). Again, the glucose disposal curves of obese Jnk1−/− mice were indistinguishable from those of lean animals. Integration of the area under the glucose disposal curves (AUC) illustrated an overall difference of 40% between Jnk1+/+ and Jnk1−/− mice (FIG. 8F). IGTT also revealed a higher degree of hyperglycemia in obese Jnk1+/+ animals throughout the experiment than in obese Jnk1−/− mice (FIG. 8G). In this test, however, the insulin responses recorded in obese Jnk1−/− mice did not reach those of lean controls, especially in the early phases, indicating residual insulin resistance. In IGTT, quantitation of the AUC illustrated an overall difference of 27% between Jnk1+/+ and Jnk1−/− mice (FIG. 8H). Interestingly, increased responsiveness in IGTT was even evident in lean Jnk1−/− mice at the early phase of the experiment. In contrast, obese Jnk2−/− animals exhibited marked insulin resistance in both IITT (FIGS. 8I and 8J) and IGTT (FIGS. 8K and 8L). The response curves of obese Jnk2−/− mice were essentially identical to those of obese wild type animals. Both tests confirmed that the inhibition of Jnk1 gene or gene product dramatically reduces the development of insulin resistance associated with dietary obesity.

Figure 11A:
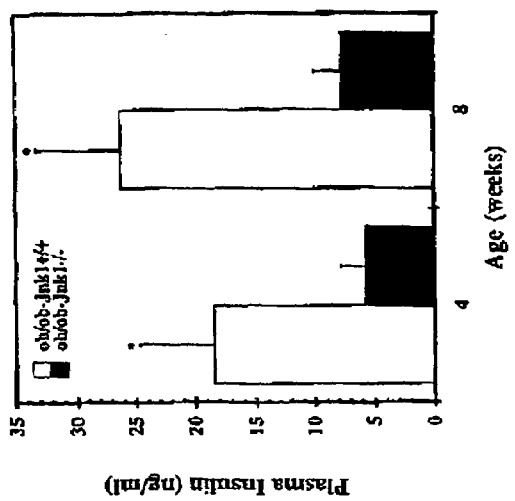
FIGS. 11A–C are bar graphs showing body weight and glucose homeostasis in Jnk1+/+ and Jnk1−/−ob/ob mice.
Figure 11B:
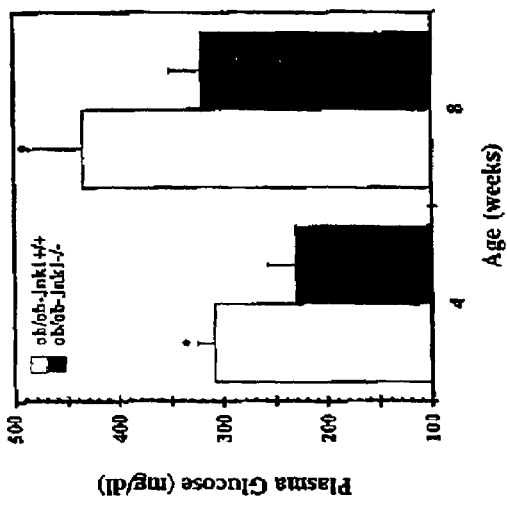
Figure 11C:
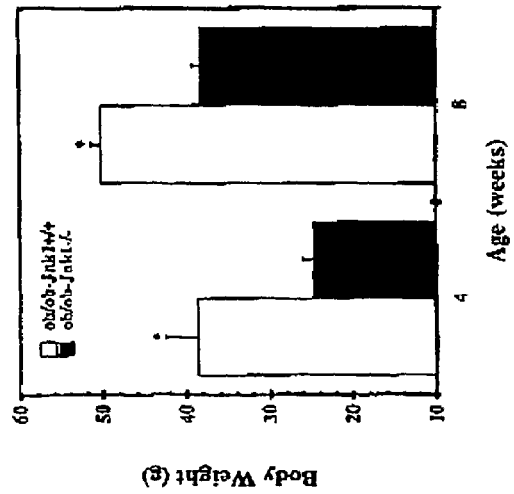

Genetically obese mice (ob/ob) with targeted mutations in Jnk1 gene were generated to test the action of JNK1 in a different and more severe model of obesity. This experiment included two additional generations of backcrossing into the C57Bl/6 genetic background. Ob/ob mice developed early onset and severe obesity (FIG. 11A). In contrast, the extent of weight gain was significantly lower in ob/ob-Jnk1−/− mice than in ob/ob-Jnk1+/+animals. Furthermore, at both 4- and 8-weeks of age the blood glucose levels were significantly lower in the ob/ob-Jnk1−/− mice compared to ob/ob-Jnk1+/+ animals (FIG. 11B). The ob/ob-Jnk1+/+ animals also displayed a severe and progressive hyperinsulinemia during the course of the study (18.4±6.2 and 26.4±7.1 ng/ml at 4 and 8 weeks of age, respectively; FIG. 11C). However, the ob/ob-Jnk1−/− displayed significantly lower plasma insulin levels throughout the study (5.7±2.1 and 7.7±2.3 ng/ml at 4 and 8 weeks of age, respectively; FIG. 11C) compared to the ob/ob animals with functional JNK1. IITT analysis also demonstrated significantly increased insulin sensitivity in ob/ob-Jnk1−/− compared to ob/ob-Jnk1+/+ animals. These experiments demonstrated that the effects of JNK1-deficiency on obesity and insulin resistance were not dependent on leptin and that inhibition of JNK1 prevents weight gain. The data indicate that inhibition of JNK1 prevents the development of insulin resistance even under conditions of severe obesity.

Figures 12A, 12B, 12C:
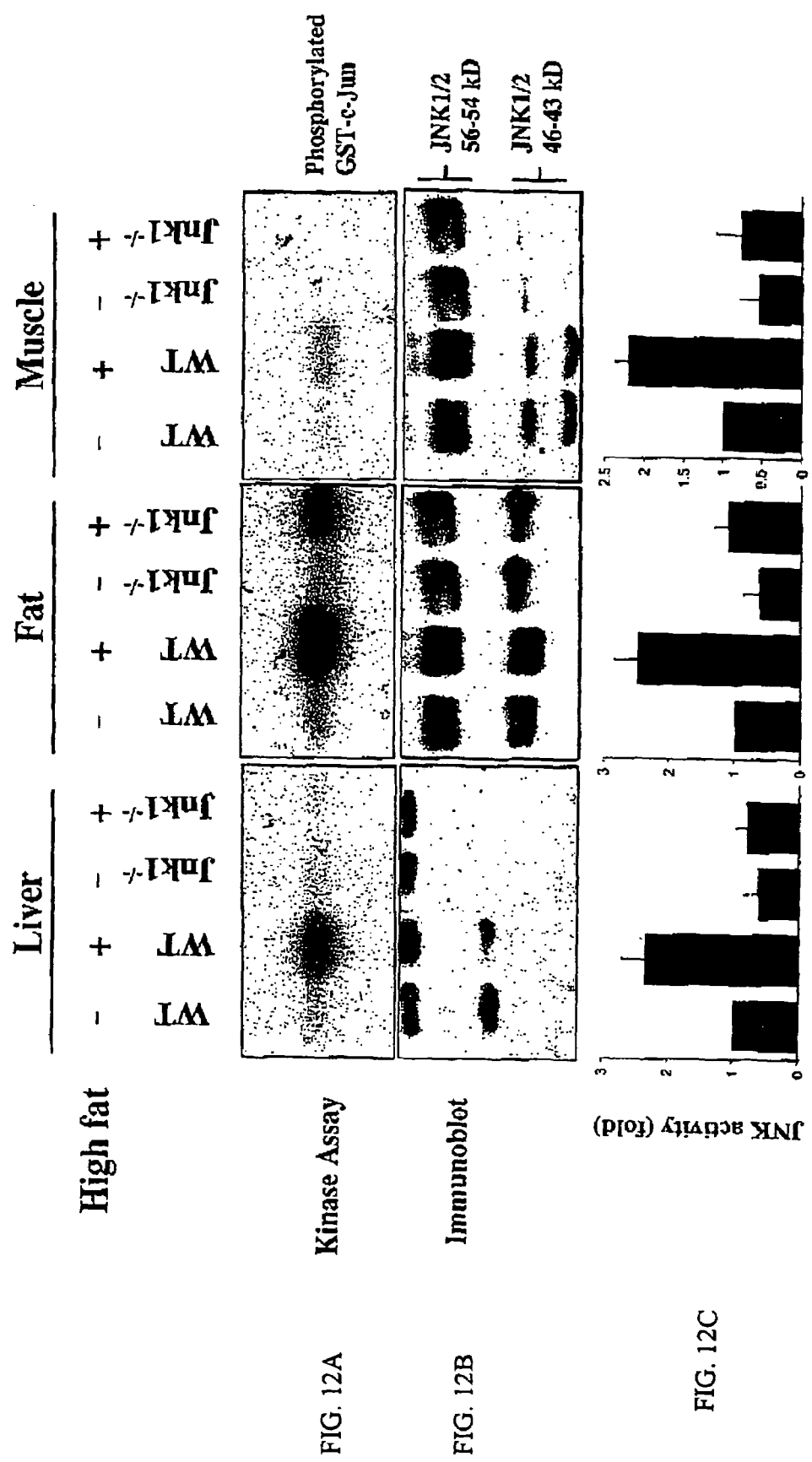
FIGS. 12A–G show JNK activity and insulin signaling in JNK1 deficient mice.

The sharp contrast in the behaviors of Jnk1−/− and Jnk2−/− animals in the context of obesity and type 2 diabetes is intriguing. In many but not all functions mediated by JNK, redundancy and molecular compensation have been observed. To seek a mechanistic explanation for the unique involvement of JNK1 isoforms in obesity-related insulin resistance, total JNK activity was measured in liver, muscle and adipose tissues of obese Jnk1−/− and Jnk2−/− mice and compared to obese wild type controls. These experiments demonstrated that JNK1-deficiency significantly reduces the obesity-induced increase in total JNK activity at all sites examined (FIGS. 12A–C). No such reduction was observed in Jnk2−/− mice. Similar observations were also made following treatment of wild type, Jnk1−/− and Jnk2−/− mice with lipopolysaccharide and using wild type, Jnk1−/− and Jnk2−/− mouse embryo fibroblasts. Thus, the JNK1 isoforms account for most, if not all, of the increased total JNK activity in the target tissues relevant for obesity-induced insulin resistance.

Mechanisms of Protection Against Development of Insulin Resistance

Experiments were carried out to elucidate molecular mechanisms by which JNK1 inhibition reduces or slows the development of insulin resistance. Many aspects of insulin signaling are defective in obesity-diabetes syndromes, including changes in insulin-sensitive glucose transporters, alterations in the secreted proteins interfering with insulin action and reduced signaling output of the insulin receptor (IR). Significant alterations in expression of the Glut1 glucose transporter were not detected in either muscle or adipose tissue, but Glut4 expression in muscle was mildly elevated in obese Jnk1−/− mice compared to obese Jnk1+/+ controls. This change was not apparent in adipose tissue. Hence regulation of glucose transporters is not likely to be a major contributor to the observed phenotype.

A more direct involvement of JNK in insulin signaling was suggested to be at the level of IRS-1 serine phosphorylation, which uncouples this important adaptor protein from insulin receptor thereby reducing IRS-1 tyrosine phosphorylation and insulin receptor signaling. Inhibitory serine phosphorylation of IRS-1 has been shown to be a mechanism for both TNF-α and FFA-induced insulin resistance. Experiments were carried out to determine whether this mechanism is involved in obesity-induced insulin resistance in vivo, and elucidate a mechanistic explanation for the protective effect of the JNK1 inhibition.

In vivo measurement of insulin receptor and IRS-1 phosphorylation was carried out as follows. After an overnight fast, mice were anaesthetized and 25 mIU/kg insulin (Eli Lilly) or an equal volume of vehicle were administered through the portal vein. Tissues were collected 120 seconds after injection in liquid nitrogen. IRS-1 serine phosphorylation was studied in livers collected from mice without any treatment. Protein extracts from the tissue samples were prepared using standard methods. Protein extracts (1 mg) were immunoprecipitated for 3 hours at 4° C. with 1 μg/ml rabbit anti-IR (Santa Cruz, Calif.) or 4 μg/mg anti-IRS-1 (Upstate Biotechnology, Lake Placid, N.Y.) antibodies. Immune complexes were collected, washed, electrophoresed and transferred to nitrocellulose membranes. Immunoblot analysis was performed using a 1:2000 dilution of a monoclonal anti-phosphotyrosine (Santa Cruz, Calif.), 1:2000 dilution of polyclonal anti-IR (Santa Cruz, Calif.) or 1 μg/mg polyclonal anti-IRS-1 or anti-IRS-1-pSer307 antibodies (Upstate Biotechnology, Lake Placid, N.Y.), followed by 1:2000 dilution of horse radish peroxidase-conjugated anti-mouse or anti-rabbit IgG secondary antibodies (Amersham Pharmacia Biotech Inc., Piscataway, N.J.) for detection.

Figure 12E:
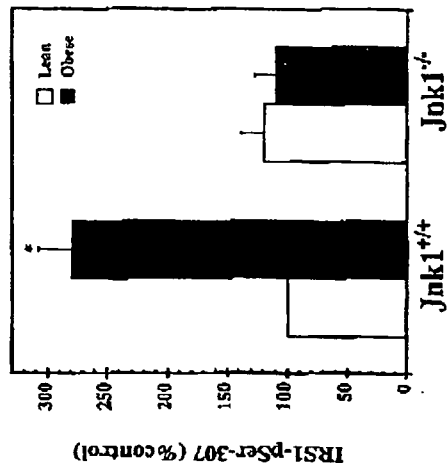
Figure 12G:
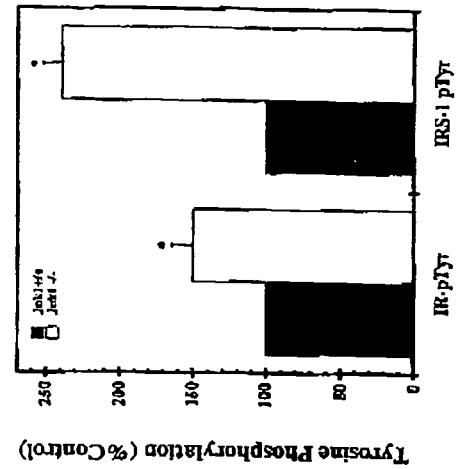
Figure 12D:
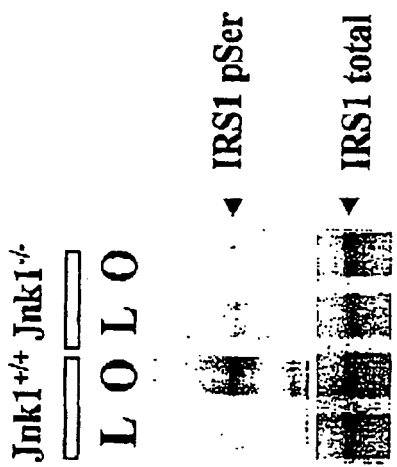
Figure 12F:
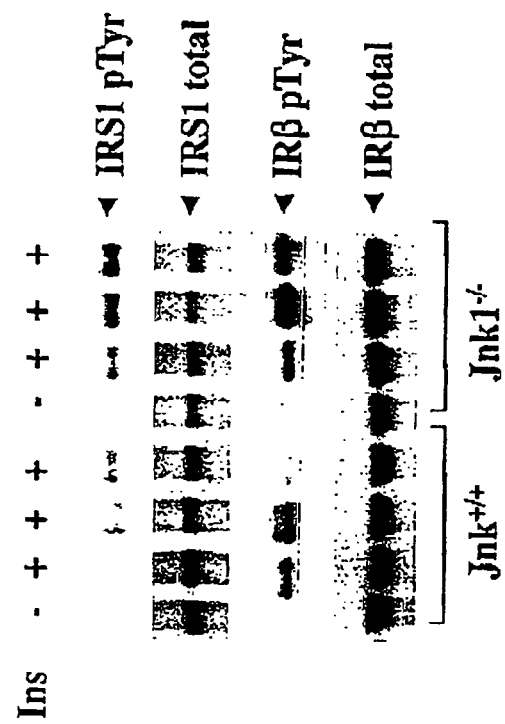

JNK-mediated IRS was phosphorylated in the liver tissue of lean and obese, Jnk1+/+ and Jnk1−/− mice was evaluated, and the level of phosphorylation analyzed using a phospho-specific antibody. Examination of IRS-1 phosphorylation at serine 307, revealed that the extent of serine 307 phosphorylation was markedly increased in wild type obese mice relative to the lean controls (FIGS. 12D–E). Most importantly, no such increase could be detected in obese Jnk1−/− mice demonstrating that serine 307 of IRS-1 is a relevant target for JNK action in vivo (FIGS. 12D–E). The extent of insulin-induced IRS-1 tyrosine phosphorylation was strongly enhanced in the livers of obese Jnk1−/− mice in comparison to obese Jnk1+/+ controls. An improvement in insulin-induced phosphorylation of the 95-kD b subunit of IR in Jnk1−/− mice was also observed (FIGS. 12F–G). Nevertheless, the increase in IRS-1 tyrosine phosphorylation was far more dramatic and consistent with reduced serine phosphorylation. These results indicate that the reduction in or absence of JNK1 enhances IR signaling capacity of the IR, at least in part, through its effects on IRS-1 phosphorylation.

The data described herein provide evidence that obesity is associated with abnormally elevated JNK activity, predominantly JNK1 activity and that inhibition of JNK1 activity protects against the development of insulin resistance. Importantly, JNK1 provides a critical link between obesity and insulin resistance in the mouse and its ablation prevents obesity-induced insulin resistance in two different models. One mechanism for JNK action involves the phosphorylation of IRS-1 at serine 307, a site where phosphorylation causes the uncoupling of IRS-1 from IR.

The data provide strong evidence that JNK1 is a critical component of the biochemical pathway responsible for obesity-induced insulin resistance in two in vivo models. There is also genetic evidence suggesting that the JNK scaffold protein JIP1 is involved in type 2 diabetes in humans. Selective inhibition of JNK1 activity is a novel approach for the treatment of obesity, insulin resistance and type 2 diabetes.

JNK1 and Accumulation of Fat in Liver Tissue

Excessive fat accumulation in liver tissue is termed fatty liver or steatosis. Fatty liver with liver inflammation is called or steatohepatitis. Steatosis and steatohepatitis can be caused by alcohol and other drugs and can also occur in patients with diabetes mellitus. Steatohepatitis not caused by alcohol is sometimes referred to as non-alcoholic steatohepatitis or "NASH". Most people who do not abuse alcohol and have fatty liver are obese. The patient is usually 10% or more above ideal body weight. Steatohepatitis can lead to scarring of the liver and cirrhosis, which may be life-threatening.

Figure 9B:
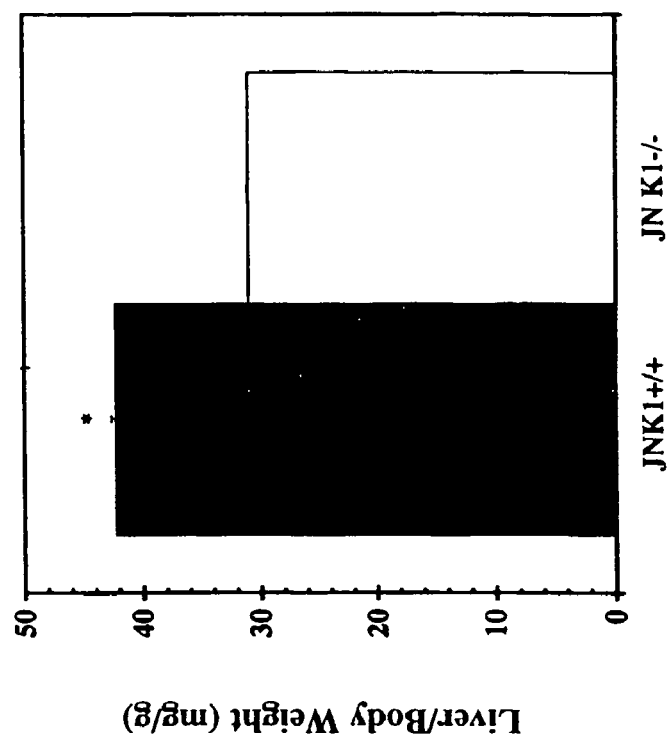
FIGS. 9A and 9B are bar graphs showing a reduction in hepatomegaly in Jnk−/− mice.
Figure 9A:
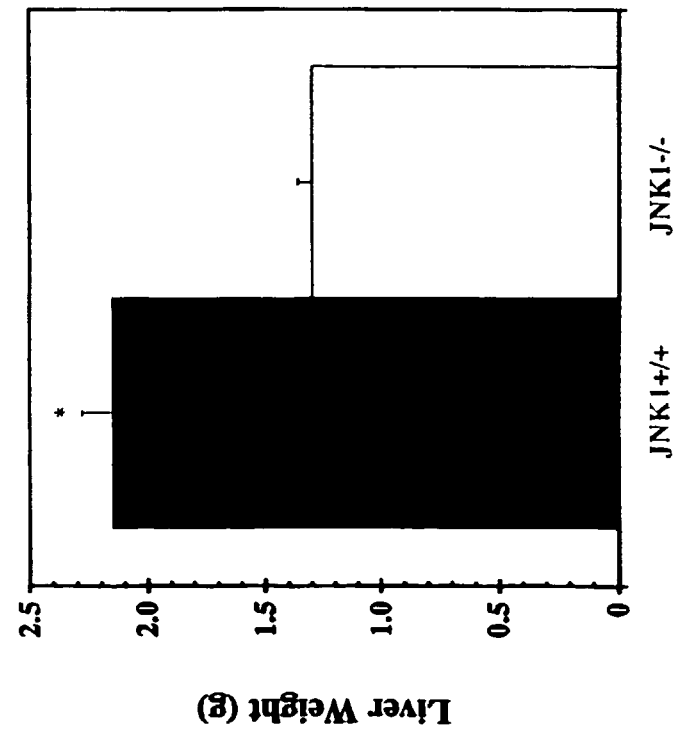
Figure 10C:
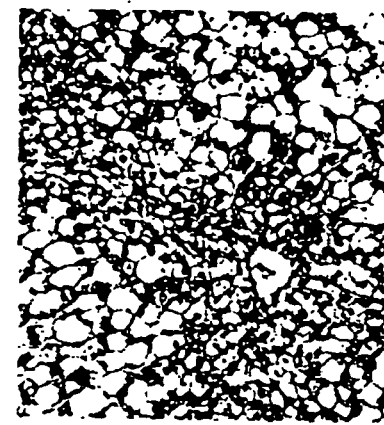
FIGS. 10A–F are photomicrographs of liver tissue sections. Tissue sections shown in FIGS. 10A–C were stained with a standard eosin hematoxylin stain to visual tissue architecture. Tissue sections shown in FIGS. 10D–F were stained with Oil-Red-O to visualize fat deposits. Dark areas in the images shown in FIGS. 10D–F represent fat deposits. The amount of fat accumulation in liver tissue of JNK1-deficient mice was greated reduced compared to the amount observed in WT or JNK2-deficient mice.
Figure 10B:
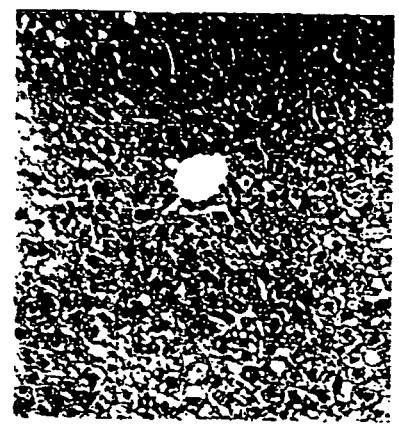
Figure 10A:
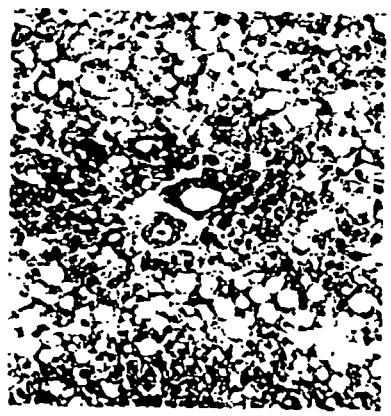
Figure 10F:
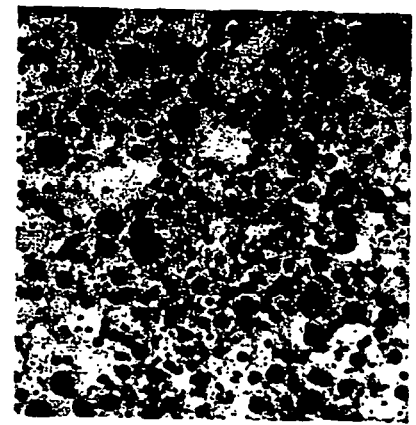
Figure 10E:
Figure 10D:
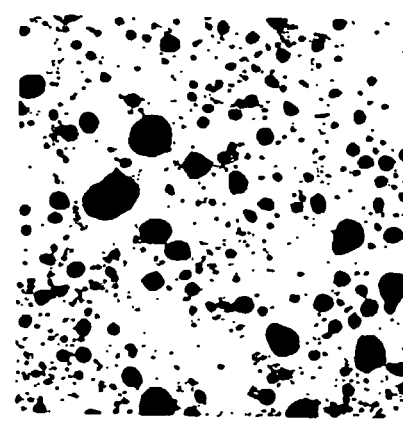

The role of JNK in development of fatty liver was evaluated. JNK1- and JNK2-deficient mice as well as wild type control mice were fed a high fat diet (55% fat) for 20 weeks. Liver tissue was excised and assayed. Gross liver weight was determined, and tissue sections were stained to visualize fat deposition. FIGS. 9A–9B show that liver weight is reduced in JNK1-deficient mice compared to JNK wild type mice. Liver tissue sections were stained with eosin/hematoxylin to visualize the tissue architecture and with Oil-Red O to visualize fat deposits. FIGS. 10A–F demonstrate a striking reduction in the amount of fat accumulation in liver tissue from JNK1-deficient mice compared to JNK2-deficient and JNK wild type mice. The data indicate that inhibition of JNK1 results in decreased fat accumulation in liver tissue and that contacting liver tissue with a compound that preferentially inhibits JNK1 protects against development of fatty liver disease.

Other embodiments are within the following claims.

What is claimed is:

1. A method of treating insulin resistance in a mammal, comprising administering to said mammal an inhibitor of NH2-terminal Jun Kinase (JNK), wherein said inhibitor is SP600125.

2. The method of claim 1, wherein said inhibitor binds to an ATP binding site in JNK.

3. The method of claim 1, wherein said inhibitor binds to a catalytic domain of JNK.

4. The method in claim 1, wherein said JUN is JNK1.

5. The method in claim 1, wherein said JUN is JNK2.

6. The method in claim 1, wherein said JUN is JNK1 and JNK2.

7. The method of claim 1, wherein said insulin resistance is associated with a metabolic disorder.

8. The method of claim 7, wherein said metabolic disorder is diabetes mellitus or obesity.

9. A method of improving insulin sensitivity, comprising administering to a mammal an inhibitor of a NH2-terminal Jun Kinase (JNK), wherein said inhibitor is SP600125.

10. A method of improving insulin sensitivity, comprising administering a therapeutically effective amount to said individual an inhibitor of a NH2-terminal Jun Kinase (JNK), wherein said inhibitor is SP600125.

* * * * *

UNITED STATES PATENT AND TRADEMARK OFFICE
CERTIFICATE OF CORRECTION

PATENT NO. : 7,232,897 B2  
APPLICATION NO. : 10/475505  
DATED : June 19, 2007  
INVENTOR(S) : Gokhan S. Hotamisligil et al.

It is certified that error appears in the above-identified patent and that said Letters Patent is hereby corrected as shown below:

Please insert the following text at column 1, line 4:

GOVERNMENT SUPPORT

This invention was made with government support under DK52539, ES04151, and ES06376 awarded by the National Institutes of Health and DE-FG03-86ER-60429 awarded by the U.S. Department of Energy. The government has certain rights in the invention.

Signed and Sealed this

Thirtieth Day of December, 2008

JON W. DUDAS  
*Director of the United States Patent and Trademark Office*